United States Patent
de Freitas et al.

(10) Patent No.: US 12,171,825 B2
(45) Date of Patent: Dec. 24, 2024

(54) VACCINE AGAINST INFECTIOUS BRONCHITIS

(71) Applicant: Zoetis Services LLC, Parsippany, NJ (US)

(72) Inventors: Carla Maria Batista de Freitas, Campinas (BR); Maria Carolina Ferreira dos Santos, Campinas (BR); Paul Joseph Dominowski, Kalamazoo, MI (US); Harmen Jacob Geerligs, AR Weesp (NL)

(73) Assignee: Zoetis Services LLC, Parsippany, NJ (US)

( * ) Notice: Subject to any disclaimer, the term of this patent is extended or adjusted under 35 U.S.C. 154(b) by 119 days.

(21) Appl. No.: 17/374,399

(22) Filed: Jul. 13, 2021

(65) Prior Publication Data

US 2022/0175911 A1 Jun. 9, 2022

Related U.S. Application Data

(62) Division of application No. 16/309,216, filed as application No. PCT/US2017/035105 on May 31, 2017, now Pat. No. 11,103,573.

(60) Provisional application No. 62/365,419, filed on Jul. 22, 2016, provisional application No. 62/344,598, filed on Jun. 2, 2016.

(51) Int. Cl.

| | |
|---|---|
| *A61K 39/155* | (2006.01) |
| *A61K 39/12* | (2006.01) |
| *A61K 39/15* | (2006.01) |
| *A61K 39/17* | (2006.01) |
| *A61K 39/215* | (2006.01) |
| *A61K 39/265* | (2006.01) |
| *A61K 39/39* | (2006.01) |
| *A61K 39/00* | (2006.01) |

(52) U.S. Cl.
CPC ............ *A61K 39/155* (2013.01); *A61K 39/12* (2013.01); *A61K 39/15* (2013.01); *A61K 39/17* (2013.01); *A61K 39/215* (2013.01); *A61K 39/265* (2013.01); *A61K 39/39* (2013.01); *A61K 2039/552* (2013.01); *A61K 2039/55561* (2013.01); *A61K 2039/55566* (2013.01); *A61K 2039/70* (2013.01); *C12N 2720/10034* (2013.01); *C12N 2720/12234* (2013.01); *C12N 2760/18134* (2013.01); *C12N 2760/18334* (2013.01); *C12N 2770/20034* (2013.01)

(58) Field of Classification Search
None
See application file for complete search history.

(56) References Cited

U.S. PATENT DOCUMENTS

| | | | |
|---|---|---|---|
| 7,488,790 B2 | 2/2009 | Dupire et al. | |
| 10,117,921 B2 | 11/2018 | Dominowski et al. | |
| 2011/0097353 A1* | 4/2011 | Sellers ..................... | C12N 7/00 |
| | | | 435/235.1 |
| 2011/0123560 A1 | 5/2011 | Rodenberg et al. | |
| 2013/0195910 A1 | 8/2013 | Harn et al. | |
| 2015/0086610 A1 | 3/2015 | Davis et al. | |

FOREIGN PATENT DOCUMENTS

| | | | | |
|---|---|---|---|---|
| CN | 102038949 A | * | 5/2011 | |
| CN | 101111261 A | * | 3/2013 | ......... A61K 39/0266 |
| EP | 2471926 A2 | * | 7/2012 | ............. A61K 39/12 |
| WO | WO 2005/063284 A1 | | 7/2005 | |
| WO | WO 2005/089795 A2 | | 9/2005 | |
| WO | WO-2010017440 A1 | * | 2/2010 | ............. A61K 39/12 |
| WO | WO 2012/089800 A1 | | 7/2012 | |
| WO | WO-2014186291 A1 | * | 11/2014 | ........... A61K 39/008 |
| WO | WO 2015/042369 A2 | | 3/2015 | |

OTHER PUBLICATIONS

WIPO translation of CN101111261A (Year: 2013).*
WIPO translation of CN102038949A (Year: 2011).*
Bragg et al., "Change in the incidences of the different serovars Haemophilus paragallinarum in South Africa: a possible explanation for vaccination failures," Onderstepoort Journal of Veterinary Research, 63: 217-226 (Year: 1996).*
Anonymous, Summary of Product Characteristics for Nobilis RT+IBmulti+G+ND (AT, BE, DE, EL, ES, IE, IT, LU, NL, PT, UK), Nobilis RT-IBmulti-G-ND (DK) and Nobilis RT Repro (FR), May 1, 2009.
Anonymous, Annex I, Summary of Product Characteristics for Nobilis IB Primo QX lyophilisate and solvent for oculonasal suspension for chickens and for Nobilis IB Primo QX lyophilisate for oculonasal suspension for chickens, Sep. 4, 2014.
Zsofia Benyeda, et al., "Comparison of the pathogenicity of QX-like, M41 and 793/B infectious bronchitis strains from different pathological conditions," Avian Pathology (Dec. 2009) 38(6), pp. 449-456.
Arshud Dar, et al., "CpG Oligodeoxynucleotides Activate Innate Immune Response that Suppresses Infectious Bronchitis Virus Replication in Chicken Embryos," Avian Diseases, 53:261-267, 2009.
Paul Wigley, (Jun. 2017) Immunology of Birds. In: eLS. John Wiley & Sons, Ltd: Chichester. DOI: 10.1002/9780470015902.a0026259.
B. Vleugels, et al., "Research Note, Stimulatory Effect of CpG Sequences on Humoral Response in Chickens," 2002 Poultry Science 81, pp. 1317-1321.
X.P. Ioannou, et al., "CpG-containing oligodeoxynucleotides, in combination with conventional adjuvants, enhance the magnitude and change the bias of the immune responses to a herpesvirus glycoprotein," Vaccine 21 (2002), pp. 127-137.

(Continued)

*Primary Examiner* — M Franco G Salvoza
(74) *Attorney, Agent, or Firm* — Vyacheslav Vasilyev

(57) ABSTRACT

Poultry vaccines against infectious bronchitis and Turkey Rhinotracheitis are provided. The vaccines are adjuvanted with oil emulsion containing an immunostimulatory oligonucleotide. The methods of using the vaccines are also provided.

17 Claims, No Drawings

Specification includes a Sequence Listing.

(56) References Cited

OTHER PUBLICATIONS

Theo Jansen, et al., Structure- and oil type-based efficacy of emulsion adjuvants, Vaccine 24 (2006), pp. 5400-5405.
Zhang Linghua, et al., "Vaccination with Newcastle disease vaccine and CpG oligodeoxynucleotides induces specific immunity and protection against Newcastle disease virus in SPF chicken," Veterinary Immunology and Immunopathology 115 (2007) pp. 216-222.
Yimeng Wang, et al., "Immunoadjuvant effects of bacterial genomic DNA and CpG oligodeoxynucleotides on avian influenza virus subtype H5N1 inactivated oil emulsion vaccine in chicken," Research in Veterinary Science 86 (2009), pp. 399-405.
Anonymous, Summary of Product Characteristics, Gallimune 407 ND+IB+EDS+ART, Feb. 2009.
G. Vahedi, et al., "The effect of CpG ODN on infectious bronchitis and Newcastle disease vaccines humoral immune response and phagocytosis in broilers," Global Veterinaria, 2010, vol. 4, No. 6, pp. 595-600, ref. 35.
Hebata Allah Mahgoub, "An overview of infectious bursal disease," Arch Virol (2012) 157, pp. 2047-2057.
Shishir Kumar Gupta, et al., "Toll-like receptor-based adjuvants: enhancing the immune response to vaccines against infectious diseases of chicken," Expert Rev. Vaccines 13(7), pp. 909-925 (2014).
Arshud Dar, et al., "CpG-ODNs induced changes in cytokine/chemokines genes expression associated with suppression of infectious bronchitis virus replication in chicken lungs," Veterinary Immunology and Immunopathology 160 (2014), pp. 209-217.

\* cited by examiner

SEQUENCE LISTING

```
<160> NUMBER OF SEQ ID NOS: 14

<210> SEQ ID NO 1
<211> LENGTH: 23
<212> TYPE: DNA
<213> ORGANISM: Artificial Sequence
<220> FEATURE:
<223> OTHER INFORMATION: CpG oligonucleotide

<400> SEQUENCE: 1
tcgtcgacga tcggcgcgcg ccg                                          23

<210> SEQ ID NO 2
<211> LENGTH: 23
<212> TYPE: DNA
<213> ORGANISM: Artificial Sequence
<220> FEATURE:
<223> OTHER INFORMATION: CpG oligonucleotide

<400> SEQUENCE: 2
tcgacgtcga tcggcgcgcg ccg                                          23

<210> SEQ ID NO 3
<211> LENGTH: 24
<212> TYPE: DNA
<213> ORGANISM: Artificial Sequence
<220> FEATURE:
<223> OTHER INFORMATION: CpG oligonucleotide

<400> SEQUENCE: 3
tcgacgtcga tcggcgcgcg ccgt                                         24

<210> SEQ ID NO 4
<211> LENGTH: 23
<212> TYPE: DNA
```

```
<213> ORGANISM: Artificial Sequence
<220> FEATURE:
<223> OTHER INFORMATION: CpG oligonucleotide
<220> FEATURE:
<221> NAME/KEY: modified_base
<222> LOCATION: (1)..(1)
<223> OTHER INFORMATION: 5'-Iodo-2'-deoxyuridine

<400> SEQUENCE: 4
ncgacgtcga tcggcgcgcg ccg                                        23

<210> SEQ ID NO 5
<211> LENGTH: 24
<212> TYPE: DNA
<213> ORGANISM: Artificial Sequence
<220> FEATURE:
<223> OTHER INFORMATION: CpG oligonucleotide
<220> FEATURE:
<221> NAME/KEY: modified_base
<222> LOCATION: (1)..(1)
<223> OTHER INFORMATION: 5'-Iodo-2'-deoxyuridine

<400> SEQUENCE: 5
ncgacgtcga tcggcgcgcg ccgt                                       24

<210> SEQ ID NO 6
<211> LENGTH: 24
<212> TYPE: DNA
<213> ORGANISM: Artificial Sequence
<220> FEATURE:
<223> OTHER INFORMATION: CpG oligonucleotide
<220> FEATURE:
<221> NAME/KEY: modified_base
<222> LOCATION: (1)..(1)
<223> OTHER INFORMATION: 5'-Iodo-2'-deoxyuridine

<400> SEQUENCE: 6
ncgacgtcga tcggcgcgcg ccgt                                       24

<210> SEQ ID NO 7
<211> LENGTH: 23
<212> TYPE: DNA
<213> ORGANISM: Artificial Sequence
<220> FEATURE:
<223> OTHER INFORMATION: CpG oligonucleotide
<220> FEATURE:
<221> NAME/KEY: modified_base
<222> LOCATION: (1)..(1)
<223> OTHER INFORMATION: 5'-Ethyl-2'-deoxyuridine

<400> SEQUENCE: 7
ncgacgtcga tcggcgcgcg ccg                                        23

<210> SEQ ID NO 8
<211> LENGTH: 24
<212> TYPE: DNA
<213> ORGANISM: Artificial Sequence
<220> FEATURE:
<223> OTHER INFORMATION: CpG oligonucleotide
<220> FEATURE:
<221> NAME/KEY: modified_base
<222> LOCATION: (1)..(1)
<223> OTHER INFORMATION: 5'-Iodo-2'-deoxyuridine

<400> SEQUENCE: 8
ncgtcgacga tcggcggccg ccgt                                       24

<210> SEQ ID NO 9
<211> LENGTH: 24
```

```
<212> TYPE: DNA
<213> ORGANISM: Artificial Sequence
<220> FEATURE:
<223> OTHER INFORMATION: CpG oligonucleotide
<220> FEATURE:
<221> NAME/KEY: modified_base
<222> LOCATION: (1)..(1)
<223> OTHER INFORMATION: 5'-Iodo-2'-deoxyuridine

<400> SEQUENCE: 9
ncgtcgacga tcggcggccg ccgt                                             24

<210> SEQ ID NO 10
<211> LENGTH: 23
<212> TYPE: DNA
<213> ORGANISM: Artificial Sequence
<220> FEATURE:
<223> OTHER INFORMATION: CpG oligonucleotide

<400> SEQUENCE: 10
tcgtcgacga tcggcgcgcg ccg                                              23

<210> SEQ ID NO 11
<211> LENGTH: 20
<212> TYPE: RNA
<213> ORGANISM: Artificial Sequence
<220> FEATURE:
<223> OTHER INFORMATION: RNA oligonucleotide

<400> SEQUENCE: 11
uuguuguugu uguuguuguu                                                  20

<210> SEQ ID NO 12
<211> LENGTH: 20
<212> TYPE: RNA
<213> ORGANISM: Artificial Sequence
<220> FEATURE:
<223> OTHER INFORMATION: RNA oligonucleotide

<400> SEQUENCE: 12
uuauuauuau uauuauuauu                                                  20

<210> SEQ ID NO 13
<211> LENGTH: 19
<212> TYPE: RNA
<213> ORGANISM: Artificial Sequence
<220> FEATURE:
<223> OTHER INFORMATION: RNA oligonucleotide

<400> SEQUENCE: 13
aaacgcucag ccaaagcag                                                   19

<210> SEQ ID NO 14
<211> LENGTH: 21
<212> TYPE: DNA
<213> ORGANISM: Artificial Sequence
<220> FEATURE:
<223> OTHER INFORMATION: DNA/RNA oligonucleotide
<220> FEATURE:
<221> NAME/KEY: misc_feature
<222> LOCATION: (11)..(17)
<223> OTHER INFORMATION: ribonucleotides

<400> SEQUENCE: 14
tcgtcgtttt guuguguttt t                                                21
```

VACCINE AGAINST INFECTIOUS BRONCHITIS

CROSS-REFERENCE TO RELATED APPLICATIONS

This application is a divisional of U.S. application Ser. No. 16/309,216 filed on Dec. 12, 2018, now allowed, which is a US National Stage entry of International Application No. PCT/US2017/035105, filed May 31, 2017, which claims the benefit of U.S. Provisional Application No. 62/344,598, filed Jun. 2, 2016 and U.S. Provisional Application No. 62/365,419, filed Jul. 22, 2016, the entire contents each of which are incorporated herein by reference.

BACKGROUND

Turkey Rhinotracheitis (TRT) is an upper respiratory tract infection of turkeys and chickens that is caused by pneumovirus. It is a highly contagious, acute disease that afflicts turkeys of all ages. The clinical symptoms of TRT infection include a marked, frequently frothy nasal discharge, rales, snicking, sneezing, and head shaking. Ocular discharge or swollen infraorbital sinuses may also be observed in infected turkeys. Antibodies to TRT virus (TRTV) have been detected in some chicken flocks (both broilers and broilers/breeders) suffering from Swollen Head Syndrome (SHS). It is postulated that TRTV plays a role in the etiology of SHS and related respiratory distress.

Infectious bronchitis (IB) is a coronavirus that only causes disease in chickens, although some other birds may be subclinically infected. Some serotypes are geographically restricted, but multiple serotypes commonly cocirculate in one geographic region. In recent years, a novel IBV genotype, the QX strain, has become increasingly common in Asia and Europe. Morbidity is commonly close to 100%. Chicks may cough, sneeze, and have tracheal rales for 10-14 days. Conjunctivitis and dyspnea may be seen, and sometimes facial swelling, particularly with concurrent bacterial infection of the sinuses. Chicks may appear depressed and huddle under heat lamps. Feed consumption and weight gain are reduced. Infection with nephropathogenic strains can cause initial respiratory signs, then later depression, ruffled feathers, wet droppings, greater water intake, and death. In layers, egg production may drop by as much as 70%, and eggs are often misshapen, with thin, soft, rough, and/or pale shells, and can be smaller and have watery albumen. In most cases, egg production and egg quality return to normal, but this may take up to 8 weeks. In most outbreaks mortality is 5%, although mortality rates are higher when disease is complicated by concurrent bacterial infection. Nephropathogenic strains can induce interstitial nephritis with high mortality (up to 60%) in young chicks. Infection of young chicks may cause permanent damage to the oviduct, resulting in layers or breeders that never reach normal levels of production.

Known vaccine strains of IB viruses have proven insufficient to protect against infectious bronchitis caused by IB-QX and IB-QX-like viruses. See WO2010017440.

Infectious bursal disease (IBD, Gumboro) is a highly contagious immunosuppressive disease of chickens that is found worldwide and causes a major economic impact on egg and meat production. IBD Vaccines form an important part of a Gumboro control strategy. The choice of vaccine to be administered depends on the type of chicken being vaccinated and the prevailing challenge situation.

Generally, inactivated antigens have been used in poultry vaccines. However, manufacturing of inactivated viruses is relatively expensive and therefore, effective vaccines containing lower level of the antigen would be desirable.

Another need in poultry vaccination is closely related to the cost of vaccination itself. It is economically advantageous to create multivalent vaccine designed to prevent multiple diseases. Such multivalent vaccines lower the cost of vaccine administration. However, due to a well-known phenomenon of antigen interference, simply mixing antigens in the same dosage forms often is not an effective approach to the creation of multivalent vaccines.

Accordingly, there is a need for poultry vaccines with lowered amounts of the antigen and/or multivalent vaccines.

SUMMARY OF INVENTION

The instant invention provides in one aspect immunogenic composition comprising an antigen component and an immunologically effective amount of an adjuvant component, wherein the antigen component comprises at least one TRT antigen and at least one IB antigen, and the adjuvant component comprises an immunostimulatory oligonucleotide, oil emulsion, and optionally, a sterol.

In certain embodiments, the at least one TRT antigen is TRT strain K.

In certain embodiments, the at least one IB antigen is at least one of IB D1466 and IB QX antigen.

In certain embodiments, the immunogenic composition of the invention is non-liposomal and/or essentially saponin-free.

In certain embodiments, the optionally present sterol is admixed with the immunostimulatory oligonucleotide.

The invention also provides a vaccine comprising an antigen component and an effective amount of the adjuvant component, wherein the adjuvant component comprises an immunostimulatory oligonucleotide and an oil emulsion, and wherein the antigen component comprises an IBD antigen.

In certain embodiments, said IBD antigen is an inactivated Lukert strain antigen, which may be present in the amount of $10^{7.5}$-$10^8$ TCID$_{50}$.

In certain embodiments, the vaccine is a multivalent vaccine comprising at least one of: an antigen derived from non-Lukert strain of IBD; an Infectious bronchitis antigen; a reovirus antigen; a Newcastle disease antigen; a Turkey rhinotracheitis antigen.

In another aspect, the invention provides a vaccine comprising an antigen component and an effective amount of the adjuvant component, wherein the adjuvant component comprises an immunostimulatory oligonucleotide and an oil emulsion, and wherein the antigen component comprises: a TRT antigen; a Newcastle antigen; an Egg Drop Syndrome (EDS) antigen; an IBK antigen; and a Coryza antigen.

In certain embodiments, the TRT antigen comprises an inactivated Turkey Rhinotracheitis virus, the Newcastle antigen comprises an inactivated Newcastle virus, the EDS antigen comprises and inactivated EDS virus, the IBK antigen comprises and inactivated IBK virus, and the Coryza antigen comprises a mixture of Coryza M, Coryza 221 and Coryza S bacterins.

In certain embodiments, the TRT antigen is present in the amount of $10^{6.00}$ TCID$_{50}$ to $10^{6.50}$ TCID$_{50}$ per dose.

In certain embodiments, said oil emulsion is a W/O emulsion.

DETAILED DESCRIPTION

Definitions:

The terms 'about' or 'approximately,' when used in connection with a measurable numerical variable, refer to the indicated value of the variable and to all values of the variable that are within the experimental error of the indicated value (e.g., within the 95% confidence interval for the mean) or within 10 percent of the indicated value, whichever is greater, unless 'about' is used in reference to time intervals in weeks where "about 3 weeks," is 17 to 25 days, and about 2 to about 4 weeks is 10 to 40 days.

The term 'consisting essentially of' and the like as applied to the adjuvant formulations of the instant invention refers to compositions which do not contain additional adjuvanting or immunomodulating agents in the amounts at which said agent exert measurable adjuvanting or immunomodulating effects.

The terms 'essentially saponin-free', 'substantially saponin-free' and the like refer to a composition that does not contain saponin in the amounts at which saponin exerts measurable adjuvanting or immunomodulating effects. In certain embodiments, essentially saponin-free compositions contain saponin in the amount insufficient to cause systemic immune response, such as fever. In certain embodiments, essentially saponin-free compositions contain no saponin or contain saponin at or below the limit of detection.

The term 'immunostimulatory molecule' refers to a molecule that generates an immune response.

The term 'parenteral administration' refers to the introduction of a substance, such as a vaccine, into a subject's body through or by way of a route that does not include the digestive tract. Parenteral administration includes subcutaneous, intramuscular, transcutaneous, intradermal, intraperitoneal, intraocular, and intravenous administration.

Purity percentage or "X percent pure" as applied to the immunostimulatory oligonucleotide preparation refers to a population of oligonucleotide molecules comprising X % of the named oligonucleotide (e.g., SEQ ID NO: 1, SEQ ID: NO: 5, SEQ ID NO: 8, etc.), and the remainder (i.e., 100% minus X %) comprises shorter fragments of the named oligonucleotide present as impurities during the manufacturing of the named sequence. Thus, if the sequence is manufactured by 3'-5' sequencing, 5'-truncations would comprise the remainder. As a non-limiting example, a preparation of 100 µg of 80% pure SEQ ID NO: 8 comprises 80 µg of SEQ ID NO: 8 and the remaining 20 µg are shorter fragments of SEQ ID NO: 8 present in the preparation.

The terms 'therapeutically effective amount' 'immunologically effective amount' and 'effective amount' refer to an amount of an antigen or an adjuvant or vaccine that would induce an immune response in a subject receiving the antigen or the adjuvant or the vaccine which is adequate to prevent or reduce signs or symptoms of disease, including adverse health effects or complications thereof, caused by infection with a pathogen, such as a virus or a bacterium. Humoral immunity or cell-mediated immunity or both humoral and cell-mediated immunity may be induced. The immunogenicity and efficacy of a vaccine in an animal may be evaluated, e.g., indirectly through measurement of antibody titers, lymphocyte proliferation assays, or directly through monitoring signs and symptoms after challenge with wild type strain. The protective immunity conferred by a vaccine can be evaluated by measuring, e.g., reduction in clinical signs such as mortality, morbidity, temperature number, overall physical condition, and overall health and performance of the subject. The amount of a vaccine that is therapeutically effective may vary depending on the particular adjuvant used, the particular antigen used, or the condition of the subject, and can be determined by one skilled in the art.

During their lives commercial laying chickens and breeder chickens are vaccinated with a wide variety of different vaccines. These vaccines mainly are attenuated live vaccines. By the time that the chickens are ready to start laying they are vaccinated with inactivated combination vaccines to booster immunity against the infectious agents against which they already received a vaccine and to induce immunity against other agents which can cause drops in the egg production or other damage during the laying period. It is important that these vaccines are capable to induce high antibody titers and that the duration of immunity is long, because the vaccines should protect during the whole laying period which lasts from an age of approximately 20 weeks to 70 weeks. In order to achieve a long duration of immunity it is necessary to formulate the antigens in an adjuvant, for example a water-in-oil (W/O) emulsion.

Thus, generally, the invention provides an immunogenic composition comprising an antigen component and an adjuvant component, wherein the antigen component comprises at least one TRT antigen and at least one IB antigen, and the adjuvant component comprises (or, in some embodiments, consists essentially of, or in other embodiments, consists of) an immunostimulatory oligonucleotide, oil emulsion, and optionally, a sterol.

Antigen Component

Different IB QX antigens are suitable for the instant invention. In certain embodiments the IB QX antigen is a whole inactivated virus. In other embodiments, the virus is a modified live virus. In yet other embodiments, subunit vaccines may be used. For example, proteins present at the surface of the virus may be suitable, including, without limitations, S protein, M protein E-protein, or any combination thereof. In the embodiments entailing the use of the inactivated whole virus, the antigen may be used in the amounts of $10^3$ to $10^{10}$ infectious units per dose, e.g., $10^4$, $10^5$, $10^6$, $10^7$ infectious units per dose. In certain embodiments, the amount of IB QX inactivated virus per dose is between about $10^5$ and about $10^8$ infectious units per dose.

In further embodiments, the antigen component comprises an IBD antigen, which, in certain embodiments, is an inactivated Lukert IBD virus.

In certain embodiments, the amount of the inactivated Lukert IBD virus is between $10^7$ and $10^8$ $TCID_{50}$ per dose, e.g., $10^{7.1}$, $10^{7.2}$, $10^{7.3}$, $10^{7.4}$, $10^{7.5}$, $10^{7.6}$, $10^{7.7}$, $10^{7.8}$, $10^{7.9}$ $TCID_{50}$ per dose.

In certain embodiments, in addition to the inactivated Lukert IBD virus, the antigen component of the vaccine comprises other antigens. For example, different strains of infectious bronchitis virus may be used, e.g., IB M41 and/or IB D1466 and/or IB D274. Alternatively or additionally, the vaccine of the instant invention may also comprise TRT, Newcastle disease (e.g., LaSota strain), EDS (egg drop syndrome), reoviruses, and infectious bursal disease virus antigens, avian influenza.

In other aspects, the invention provides a multivalent vaccine comprising a TRT antigen; a Newcastle antigen; an Egg Drop Syndrome (EDS) antigen; an IBK antigen (Infectious bronchitis viruses); and a Coryza antigen.

In certain embodiments of the invention, the TRT antigen is present in the amount of $10^{6.00}$ $TCID_{50}$ to $10^{6.50}$ $TCID_{50}$ per dose, e.g., $10^{6.00}$ $TCID_{50}$ or $10^{6.10}$ $TCID_{50}$ or $10^{6.20}$ $TCID_{50}$ or $10^{6.30}$ $TCID_{50}$ or $10^{6.40}$ $TCID_{50}$ or $10^{6.50}$ $TCID_{50}$.

Viruses used in the vaccines of this invention may be attenuated or inactivated. The methods for virus inactivation and attenuation are well known in the art. For example, the virus may be inactivated by culture passage. Methods if inactivation include, without limitations, exposure of the virus to an effective amount of an inactivation chemical selected from formalin, beta propiolactone (BPL), binary ethylenimine (BEI), or phenol.

Coryza is caused by different strains of *Haemophilus paragallinarum*. Thus, in certain embodiments, the Coryza antigen comprises one or more *Haemophilus paragallinarum* strains, e.g., strain M, strain Z, strain 221, and the like. In other embodiments, a mixture of strains representing serovars A, B, and C are used. Thus, strain 221 (Coryza 221) may be used as a Serovar A strain, strain Spross (Coryza S) may be used as a Serovar B stain, and Strain Modesto (Coryza M) may be used as a Serovar C strain.

A person of ordinary skill in the art may realize that the titer of a virus may vary depending on the methodology of virus titration, sometimes by as much as about 30%. In this disclosure, where the doses are measured as an exponent of 10, the exponent may vary by 0.2. Thus, for example the titer of $10^{6.40}$ TCID$_{50}$ may encompass the values between $10^{6.20}$ TCID$_{50}$ and $10^{6.60}$ TCID$_{50}$. The same idea applies to ranges of titers. For example, the titer of $10^{6.00}$ TCID$_{50}$-$10^{6.50}$ TCTD$_{50}$ encompasses the range from $10^{5.80}$ TCID$_{50}$ to $10^{6.70}$ TCTD$_{50}$.

In other embodiments, other antigens may be used in addition to the antigens recited above, e.g., *Salmonella enteritidis, Salmonella typhimurium, Mycoplasma gallisepticum, Salmonella gallinarum, Pasteurella multocida*. Similarly to virus inactivation, bacteria can also be inactivated by, for example, exposure to an effective amount of an inactivation chemical selected from formalin, beta propiolactone (BPL), binary ethylenimine (BEI), or phenol.

Adjuvant Component

Generally, the adjuvant component used in the immunogenic composition of the invention comprises immunostimulatory oligonucleotide, oil, and optionally, surfactant(s). In certain embodiments, the adjuvant component is free or essentially free of saponins and/or ISCOMs.

In certain embodiments, the adjuvant component consists essentially of immunostimulatory oligonucleotide, oil, and optionally, surfactant(s). In certain embodiments, the adjuvant component consists of immunostimulatory oligonucleotide, oil, and optionally, surfactant(s).

Suitable immunostimulatory oligonucleotides include ODN (DNA-based), ORN (RNA-based) oligonucleotides, or chimeric ODN-ORN structures, which may have modified backbone including, without limitations, phosphorothioate modifications, halogenations, alkylation (e.g., ethyl- or methyl-modifications), and phosphodiester modifications. In some embodiments, poly inosinic-cytidylic acid or derivative thereof (poly I:C) may be used.

CpG oligonucleotides are characterized by the presence of an unmethylated CG dinucleotide in specific base-sequence contexts (CpG motif). (Hansel T T, Barnes P J (eds): New Drugs for Asthma, Allergy and COPD. Prog Respir Res. Basel, Karger, 2001, vol 31, pp 229-232, which is incorporated herein by reference). These CpG motifs are not seen in eukaryotic DNA, in which CG dinucleotides are suppressed and, when present, usually methylated, but are present in bacterial DNA to which they confer immunostimulatory properties.

In selected embodiments, the adjuvants of the instant invention utilize a so-called P-class immunostimulatory oligonucleotide, more preferably, modified P-class immunostimulatory oligonucleotides, even more preferably, E-modified P-class oligonucleotides. P-class immunostimulatory oligonucleotides are CpG oligonucleotides characterized by the presence of palindromes, generally 6-20 nucleotides long. The P-Class oligonucleotides have the ability to spontaneously self-assemble into concatamers either in vitro and/or in vivo. These oligonucleotides are, in a strict sense, single-stranded, but the presence of palindromes allows for formation of concatamers or possibly stem-and-loop structures. The overall length of P-class immunostimulatory oligonucleotides is between 19 and 100 nucleotides, e.g., 19-30 nucleotides, 30-40 nucleotides, 40-50 nucleotides, 50-60 nucleotides, 60-70 nucleotides, 70-80 nucleotides, 80-90 nucleotides, 90-100 nucleotides.

In one aspect of the invention the immunostimulatory oligonucleotide contains a 5' TLR activation domain and at least two palindromic regions, one palindromic region being a 5' palindromic region of at least 6 nucleotides in length and connected to a 3' palindromic region of at least 8 nucleotides in length either directly or through a spacer.

The P-class immunostimulatory oligonucleotides may be modified according to techniques known in the art. For example, J-modification refers to iodo-modified nucleotides. E-modification refers to ethyl-modified nucleotide(s). Thus, E-modified P-class immunostimulatory oligonucleotides are P-class immunostimulatory oligonucleotides, wherein at least one nucleotide (preferably 5' nucleotide) is ethylated. Additional modifications include attachment of 6-nitro-benzimidazol, O-Methylation, modification with proynyl-dU, inosine modification, 2-bromovinyl attachment (preferably to uridine).

The P-class immunostimulatory oligonucleotides may also contain a modified internucleotide linkage including, without limitations, phosphodiesther linkages and phosphorothioate linkages. The oligonucleotides of the instant invention may be synthesized or obtained from commercial sources.

P-Class oligonucleotides and modified P-class oligonucleotides are further disclosed in published PCT application no. WO2008/068638, published on Jun. 12, 2008. Suitable non-limiting examples of modified P-class immunostimulatory oligonucleotides are provided below (In SEQ ID NOs 1-10, "*" refers to a phosphorothioate bond and "-" refers to a phosphodiester bond). In SEQ ID NOs 11-14, all bonds are phosphodiester bonds.

```
                                                SEQ ID NO: 1
5' T*C-G*T*C-G*A*C-G*A*T*C-G*G*C*G*C-G*C*G*C*C*

G 3'
```

```
                                                SEQ ID NO: 2
5' T*C-G*A*C*G*T*C*G*A*T*C*G*G*C*G*C*G*C*G*C*C*

G 3'
```

```
                                                SEQ ID NO: 3
5' T*C*G*A*C*G*T*C*G*A*T*C*G*G*C*G*C*G*C*G*C*C*

G*T 3'
```

```
                                                SEQ ID NO: 4
5' JU*C-G*A*C*G*T*C*G*A*T*C*G*G*C*G*C*G*C*G*C*

C*G 3'
```

-continued

```
                                                    SEQ ID NO: 5
5' JU*C-G*A*C*G*T*C*G*A*T*C*G*G*C*G*C*G*C*G*C*
C* G*T 3'

SEQ ID NO: 6
5' JU*C*G*A*C*G*T*C*G*A*T*C*G*G*C*G*C*G*C*G*C*
C* G*T 3'

SEQ ID NO: 7
5' EU*C-G*A*C*G*T*C*G*A*T*C*G*G*C*G*C*G*C*G*C*
C*G 3'

SEQ ID NO: 8
5' JU*C-G*T*C*G*A*C*G*A*T*C*G*G*C*G*C*G*C*G*C*
C* G*T 3'

SEQ ID NO: 9
5' JU*C*G*T*C*G*A*C*G*A*T*C*G*G*C*G*G*C*C*G*C*
C* G*T 3'

SEQ ID NO: 10
5' T*C-G*T*C-G*A*C-G*A*T*C-G*G*C*G*C_G*C*G*C*
C*G 3'

SEQ ID NO: 11
5'-UUGUUGUUGUUGUUGUUGUU-3'

SEQ ID NO: 12
5'-UUAUUAUUAUUAUUAUUAUU-3'

SEQ ID NO: 13
5'-AAACGCUCAGCCAAAGCAG-3'

SEQ ID NO: 14
5'-dTdCdGdTdCdGdTdTdTdTrGrUrUrGrUrGrUdTdTdTdT-3'
```

The immunostimulatory oligonucleotides of the instant invention may be chemically synthesized. Further, the immunostimulatory oligonucleotides may be used at about 60% purity (homogeneity) or greater (e.g., about 65%, about 70%, about 75%, about 80%, about 85%, about 90%, about 95%, about 98%, or 100% purity)

The amount of P-class immunostimulatory oligonucleotide for use in the adjuvant compositions depends upon the nature of the P-class immunostimulatory oligonucleotide used and the intended species.

Sterols share a common chemical core, which is a steroid ring structure[s], having a hydroxyl (OH) group, usually attached to carbon-3. The hydrocarbon chain of the fatty-acid substituent varies in length, usually from 16 to 20 carbon atoms, and can be saturated or unsaturated. Sterols commonly contain one or more double bonds in the ring structure and also a variety of substituents attached to the rings. Sterols and their fatty-acid esters are essentially water insoluble. In view of these chemical similarities, it is thus likely that the sterols sharing this chemical core would have similar properties when used in the vaccine compositions of the instant invention. Sterols are well known in the art and can be purchased commercially. For example cholesterol is disclosed in the Merck Index, 12th Ed., p. 369. Suitable sterols include, without limitations, β-sitosterol, stigmasterol, ergosterol, ergocalciferol, cholesterol, and derivatives thereof such as, for example DC-Cholesterol (3β-[N-(Dimethylaminoethane)carbamoyl]cholesterol).

Multiple oils and combinations thereof are suitable for use of the instant invention. These oils include, without limitations, animal oils, vegetable oils, as well as non-metabolizable oils. Non-limiting examples of vegetable oils suitable in the instant invention are corn oil, peanut oil, soybean oil, coconut oil, olive oil, and phytosqualane. Non-limiting example of animal oils is squalane. Suitable non-limiting examples of non-metabolizable oils include light mineral oil, straight chained or branched saturated oils, ramified oils, and the like.

In a set of embodiments, the oil used in the adjuvant formulations of the instant invention is a light mineral oil. As used herein, the term "mineral oil" refers to a mixture of liquid hydrocarbons obtained from petrolatum via a distillation technique. The term is synonymous with "liquefied paraffin", "liquid petrolatum" and "white mineral oil." The term is also intended to include "light mineral oil," i.e., oil which is similarly obtained by distillation of petrolatum, but which has a slightly lower specific gravity than white mineral oil. See, e.g., Remington's Pharmaceutical Sciences, 18th Edition (Easton, Pa.: Mack Publishing Company, 1990, at pages 788 and 1323). Mineral oil can be obtained from various commercial sources, for example, J. T. Baker (Phillipsburg, Pa.), USB Corporation (Cleveland, Ohio). Preferred mineral oil is light mineral oil commercially available under the name DRAKEOL®. In another embodiment, the suitable oil comprises mineral oil MARCOL™ 52. MARCOL™ 52 is a purified mixture of liquid saturated hydrocarbons. It is a crystal clear, water-white product that contains no toxic impurities. It is obtained from petroleum by vacuum distillation with subsequent refining stages including an ultimate purification by catalytic hydrogenation.

Emulsifiers suitable for use in the present emulsions include natural biologically compatible emulsifiers and non-natural synthetic surfactants. Biologically compatible emulsifiers include phospholipid compounds or a mixture of phospholipids. Preferred phospholipids are phosphatidylcholines (lecithin), such as soy or egg lecithin. Lecithin can be obtained as a mixture of phosphatides and triglycerides by water-washing crude vegetable oils, and separating and drying the resulting hydrated gums. A refined product can be obtained by fractionating the mixture for acetone insoluble phospholipids and glycolipids remaining after removal of the triglycerides and vegetable oil by acetone washing. Alternatively, lecithin can be obtained from various commercial sources. Other suitable phospholipids include phosphatidylglycerol, phosphatidylinositol, phosphatidylserine, phosphatidic acid, cardiolipin, phosphatidylethanolamine, lysophosphatidylcholine, lysophosphatidylserine, lysophosphatidylinositol, and lysophosphatidylethanolamine. The phospholipids may be isolated from natural sources or conventionally synthesized.

In additional embodiments, the emulsifiers used herein do not include lecithin, or use lecithin in an amount which is not immunologically effective.

Non-natural, synthetic emulsifiers suitable for use in the adjuvant formulations of the present invention include sorbitan-based non-ionic surfactants, e.g. fatty-acid-substituted sorbitan surfactants (commercially available under the name SPAN® or ARLACEL®), fatty acid esters of polyethoxylated sorbitol (TWEEN®), polyethylene glycol esters of fatty acids from sources such as castor oil (EMULFOR®); polyethoxylated fatty acid (e.g., stearic acid available under the name SIMULSOL® M-53), polyethoxylated isooctylphenol/formaldehyde polymer (TYLOXAPOL®), polyoxyethylene fatty alcohol ethers (BRIJ®); polyoxyethylene nonphenyl ethers (TRITON® N), polyoxyethylene isooctylphenyl ethers (TRITON® X). Preferred synthetic surfactants are the surfactants available under the name SPAN® and TWEEN®, such as TWEEN®-80 (Polyoxyethylene (20) sorbitan monooleate) and ARLACEL™ 83V (Sorbitan Sesquioleate)).

Generally speaking, the emulsifier(s) may be present in the vaccine composition in an amount of 0.01% to 40% by volume, preferably, 0.1% to 15%, more preferably 2% to 10%.

In a subset of embodiments, the volume percentage of the oil and the oil-soluble emulsifier together is at least 50%, e.g., 50% to 95% by volume; preferably, in an amount of greater than 50% to 85%; more preferably, in an amount from 50% to 60%, and more preferably in the amount of 55-65% v/v of the vaccine composition. Thus, for example and without limitations, the oil may be present in the amount of 45% and the lipid-soluble emulsifier would be present in the amount of greater than 5% v/v. Thus, the volume percentage of the oil and the oil-soluble emulsifier together would be at least 50%.

In yet another subset, applicable to all vaccines of the invention, volume percentage of the oil is over 40%, e.g., 40% to 90% by volume; 40% to 85%; 43% to 60%, 44-50% v/v of the vaccine composition. In certain embodiments, the emulsions contain at least 60% v/v oil phase and 40% v/v aqueous phase.

Sometimes, it is impossible or impracticable to concentrate the antigen, particularly in scaled up commercial applications, and low-concentrations of antigen solutions have to be used.

Thus in some embodiments, the vaccine compositions of the instant invention comprise the adjuvant formulations as described above, wherein the content of the oily phase in these adjuvant formulations is diluted and wherein the vaccine composition is a water-in-oil emulsion.

In practice, it is possible to create a water-in-oil emulsion wherein the oily phase is less than 50% v/v.

Briefly, first, the adjuvant formulation of the instant invention is prepared as described above. In said adjuvant formulation, the oily phase comprises over 50% v/v of the adjuvant formulation. The amounts of ingredients other than the oil and the emulsifier(s) are scaled up respectively, based on the final target concentration and desired dilution. For example, if one aims to prepare a vaccine composition where the adjuvant formulation comprises 80% v/v, the amounts of ingredients other than the oil are scaled up by the factor of 1.25 (1/0.8). The amounts of emulsifiers, if any (e.g., TWEEN®80 and/or SPAN®80) do not necessarily need to be scaled up, but preferably, the volume ratio between the oil and the emulsifier(s) is kept the same in the adjuvant formulation and in the final vaccine composition.

Antigen solution is then added to the adjuvant formulation.

Water-in-oil emulsion's integrity can be maintained as long as the dispersed spherical water droplets are not present in a more concentrated form than the maximum packing fraction for random packing of monodisperse droplets, i.e.: 0.64. See Tadros, *Emulsion Formation, Stability and Rheology*, $1^{st}$ ed. 2013, Wiley-VCH GmbH & Co KGaA. As long as the total volume fraction occupied by the aqueous droplets does not exceed 0.64, i.e.: 64% v/v. Conversely, this implies that the oily phase should not drop below 36% v/v.

In some embodiments suitable, one dose of the adjuvant would contain between about 0.1 and about 20 µg (e.g., 1-20 µg, or 5-15 µg or 8-12 µg or 10 µg) of immunostimulatory oligonucleotide, up to about 50 µg (e.g., 0.5-20 µg, or 1-10 µg) of the sterol such as cholesterol.

In certain embodiments, the adjuvant component is prepared as follows:

a) Sorbitan Sesquioleate, and cholesterol, if any, are dissolved in light mineral oil. The resulting oil solution is sterile filtered;
b) The immunostimulatory oligonucleotide and Polyoxyethylene (20) sorbitan monooleate are dissolved in aqueous phase, thus forming the aqueous solution;
c) The aqueous solution is added to the oil solution under continuous homogenization.

The immunogenic composition of the instant invention may be prepared by adding the antigen component to the aqueous phase followed by combining the aqueous phase with the oil phase. In other embodiments, the antigen component may be added to the adjuvant component after the adjuvant component is prepared.

The immunogenic composition may further comprise a pharmaceutically acceptable carrier. As used herein, "a pharmaceutically-acceptable carrier" includes any and all solvents, dispersion media, coatings, adjuvants, stabilizing agents, diluents, preservatives, antibacterial and antifungal agents, isotonic agents, adsorption delaying agents, and the like. The carrier(s) must be "acceptable" in the sense of being compatible with the other components of the compositions and not deleterious to the subject. Typically, the carriers will be sterile and pyrogen-free, and selected based on the mode of administration to be used. It is well known by those skilled in the art that the preferred formulations for the pharmaceutically acceptable carrier which comprise the compositions are those pharmaceutical carriers approved in the applicable regulations promulgated by the United States (US) Department of Agriculture or US Food and Drug Administration, or equivalent government agency in a non-US country. Therefore, the pharmaceutically accepted carrier for commercial production of the compositions is a carrier that is already approved or will be approved by the appropriate government agency in the US or foreign country.

Other components of the compositions can include pharmaceutically acceptable excipients, such as carriers, solvents, and diluents, isotonic agents, buffering agents, stabilizers, preservatives, vaso-constrictive agents, antibacterial agents, antifungal agents, and the like. Typical carriers, solvents, and diluents include water, saline, dextrose, ethanol, glycerol, oil, and the like. Representative isotonic agents include sodium chloride, dextrose, mannitol, sorbitol, lactose, and the like. Useful stabilizers include gelatin, albumin, and the like.

Administration of the Vaccine

Generally, the vaccines of the instant invention may be administered via multiple routes. Such routes are known to persons of ordinary skill in the art and include, without limitations intramuscular and subcutaneous injections.

In certain embodiments, the vaccines are administered at about 3-7 weeks (e.g., about 4-6 weeks) before the expected lay. This regimen ensures that the immunity to IB QX is developed by the time of lay and persists throughout the laying period of the vaccinated hens.

In additional embodiments, the vaccine of the instant invention is administered as a booster vaccine, to hens which have been primed. Multiple IB primers are known in the art. For example, POULVAC® IB Primer comprises a freeze-dried, Massachusetts type, live Infectious Bronchitis virus. NOBILIS® IB H120 is a live freeze-dried vaccine indicated for use as a primary vaccination of fowls against Infectious Bronchitis. This vaccine contains strain H120 type Massachusetts. Other IB primers may also be used with the vaccine of the instant invention.

The invention will further be described in the following non-limiting examples.

EXAMPLES

Example 1. Vaccine Preparation

Exemplary water-in-oil emulsion is provided in Table 1. The antigens are diluted in the water phase to which also CpG is added. The water phase comprises antigens, CpG and Thimerosal. It is mixed with the oil phase. After thorough mixing, a stable W/O emulsion is formed.

TABLE 1

Composition of a W/O emulsion.

Aq. Phase (40%): 80 mL

| Components | Stock | | Target | Quantity (mL) |
|---|---|---|---|---|
| TWWEN ® 80 | 100% | purity | 0.004 MI/dose | 1.6 |
| Thimerosal 1% | 100% | purity | 0.005 MI/dose | 2.0 |
| CpG (SEQ ID NO: 8, 65% purity) | 20000 | µg/MI | 10 µg/dose | 0.2 |
| Saline Solution + antigens | N/A | — | N/A add 0.5 MI | 76.2 |
| | | | Sub-total | 80.0 |

Oil Phase (60%) 120 MI

| Components | Stock | | Target | Quantity (g) |
|---|---|---|---|---|
| ARLACEL ™ 83V | 100% | purity | 0.239 g/dose | 95.6 |
| MARCOL ™ 52 | 100% | purity | 0.023 g/dose | 9.2 |
| | | | Sub-total | 104.8 |

Final emulsion

| Components | Stock | | Target, v/v | Volume (mL) |
|---|---|---|---|---|
| Aq. Phase (40%) | 100% | purity | 40% | 80.0 |
| Oil Phase (60%) | 100% | purity | 60% | 120.0 |
| | | | Total Volume | 200.0 mL |

Example 2. Potency Assays for IB or TRT

The inventors produced W/O emulsions containing inactivated IB M41 antigen ($10^{7.2}$ $EID_{50}$ before inactivation per dose) or inactivated TRT antigen ($10^{5.3}$ $TCID_{50}$ before inactivation per dose). These emulsions contained different quantities of CpG or no CpG (SEQ ID NO: 8, 65% purity). The emulsions were tested in a potency test in chickens. The chickens were vaccinated at an age of 4 weeks. At 5 weeks after vaccination blood samples were collected and tested for antibody titers against the antigens by ELISA.

Antibody titres against turkey rhinotracheitis (TRT) virus were determined using an enzyme-linked immunosorbent assay (ELISA) in which the antigen was coated to the wells of 96 wells micro ELISA plates. After coating standard negative and standard positive sera were added to the wells and the sera to be tested. All sera were tested in duplicate. As control all sera were tested also in duplicate in wells without antigen. Unbound antibodies were removed and the reactivity of the antibodies to the antigen was visualized by adding antibodies against the serum antibodies to which peroxidase had been conjugated. After removal of unbound conjugated antibodies, the peroxidase substrate ortho phenylene diamino+$H_2O_2$ was added. The presence of peroxidase was demonstrated by the development of a color reaction.

The results of the potency test of the TRT antigen are summarized in Table 2. In general antibody titers were satisfactory and there were no non-responders in any of the groups. There was a positive effect of CpG on the antibody titers. Best results were obtained with 10 µg CpG per dose, but also 1 µg CpG per dose had a positive effect.

TABLE 2

Antibody titers in blood samples from chickens vaccinated 5 weeks earlier at an age of 4 weeks with inactivated TRT antigen formulated in a W/O emulsion containing different quantities of CpG.
TRT $log_2$ antibody titers by ELISA

| CpG/dose | 0 µg | 1 µg | 10 µg |
|---|---|---|---|
| Individual titers expressed as $log_2$ titers | 10.53 | 12.30 | 16.03 |
| | 11.38 | 14.99 | 16.93 |
| | 7.78 | 15.27 | 12.77 |
| | 17.25 | 13.16 | 15.64 |
| | 11.47 | 15.71 | 15.20 |
| | 10.68 | 12.37 | 15.31 |
| | 14.03 | 12.40 | 17.10 |
| | 12.06 | 13.04 | 16.16 |
| | 15.21 | 15.74 | 13.92 |
| | 12.28 | | 15.84 |
| Average | 12.27 | 13.89 | 15.49 |

Also a positive effect of CpG was determined on the antibody response against IB M41, see Table 3. A dose of 1 µg CpG per dose already was sufficient to stimulate the antibody response substantially. Without CpG, 7 out of 15 chickens had an antibody response below the threshold of 2.60, whereas all chickens responded when 1 µg CpG per dose was tested. A further increase was obtained with 10 µg CpG per dose.

TABLE 3

Antibody titers in blood samples from chickens vaccinated 5 weeks earlier at an age of 4 weeks with inactivated IB M41 antigen formulated in a W/O emulsion containing different quantities of CpG.
IB antibody titers by ELISA

| Treatment group | O/W | O/W + 1 µg CpG/dose | O/W + 10 µg CpG/dose |
|---|---|---|---|
| Individual titers expressed as $Log_{10}$Titer | 3.65 | 4.06 | 3.79 |
| | 2.08 | 3.12 | 3.32 |
| | 2.49 | 3.97 | 3.89 |
| | 2.84 | 2.80 | 3.85 |
| | 0.00 | 3.14 | 3.76 |
| | 3.19 | 2.62 | 3.59 |
| | 0.00 | 3.54 | 3.59 |
| | 0.00 | 3.18 | 3.17 |
| | 2.42 | 3.36 | 3.12 |
| | 2.48 | 2.99 | 3.42 |
| | 3.33 | 3.42 | 3.94 |
| | 2.74 | 3.73 | 3.76 |
| | 2.86 | 3.18 | 4.11 |
| | 3.23 | 3.91 | 3.86 |
| | 2.83 | — | 4.13 |
| Average | 2.28 | 3.36 | 3.69 |

*Titers higher than 396 ($Log_{10}$Titer = 2.60) are considered positive by the kit.

Example 3. Potency Assays for IB, ND, EDS

Groups of 10 SPF chickens were vaccinated with 0.5 ml per dose intramuscularly at an age of 4 weeks. Blood samples for serological testing were collected at 5 weeks after vaccination. For measuring antibody titres against IB, ND and EDS, an ELISA (Idexx FlockCheck IBV antibody kit; Idexx, Maine, USA), a hemagglutination inhibition test and an ELISA (Idexx FlockCheck NCD antibody kit; Idexx, Maine, USA), respectively were used.

The vaccines contained:
IB M41: $10^{6.9}$ $EID_{50}$/dose,
Newcastle disease (ND): $10^{8.1}$ $EID_{50}$/dose,
Egg-Drop Syndrome (EDS): 256 HAu/dose,
in water in oil emulsions containing different quantities of CpG.

Groups of 10 SPF chickens were vaccinated with 0.5 ml per dose intramuscularly at an age of 4 weeks. Blood samples for serological testing were collected at 5 weeks after vaccination. For measuring antibody titres against IB, ND and EDS, an ELISA (Idexx FlockCheck IBV antibody kit; Idexx, Maine, USA), a hemagglutination inhibition test and an ELISA (Idexx FlockCheck NCD antibody kit; Idexx, Maine, USA), respectively were used.

The results for IB, ND, and EDS are shown in Tables 4-6, respectively

TABLE 4

ELISA IB antibody titers days after vaccination

| Vaccine batch | N | Geometric mean 2log | No. of responders |
|---|---|---|---|
| Not vaccinated | 10 | 3.0 | 0 (0%) |
| No CpG | 10 | 7.7 [A*] | 4 (40%) |
| 5 µg CpG/dose | 10 | 9.9 [B] | 8 (80%) |
| 2.5 µg CpG/dose | 10 | 7.3 [A] | 3 (30%) |

TABLE 5

ELISA NCD antibody titers 35 days after vaccination

| Vaccine batch | N | Geometric mean | No. of responders |
|---|---|---|---|
| Not vaccinated | 10 | 34 | 0 (0%) |
| No CpG | 10 | 12532 [A] | 10 (100%) |
| 5 µg CpG/dose | 10 | 18421 [B] | 10 (100%) |
| 2.5 µg CpG/dose | 10 | 15689 [B] | 10 (100%) |

TABLE 6

HI antibody titers to EDS 35 days after vaccination

| Vaccine batch | N | Geometric mean | No. of responders |
|---|---|---|---|
| Not vaccinated | 10 | 0 | 0 (0%) |
| No CpG | 10 | 7.7 [A] | 10 (100%) |
| 5 µg CpG/dose | 10 | 8.4 [A] | 10 (100%) |
| 2.5 µg CpG/dose | 10 | 7.8 [A] | 10 (100%) |

* Different letters in superscript mean that the differences are statistically significant.

Results and Conclusions

For IB M41 and ND there are significant differences between formulations without CpG and formulation with 5 µg CpG per dose. For ND 2.5 µg CpG per dose also improved antibody titres significantly. For EDS there were no significant differences between formulations without CpG and formulations with CpG, but numerically 5 µg CpG per dose was better than no CpG.

CpG has a stimulating effect on the antibody responses of IB M41, ND and EDS if added in a quantity of 5 µg per dose. The effect of 2.5 µg CpG per dose is limited.

Example 4. Efficacy Test

Combination vaccines were produced containing different quantities of inactivated IB QX, inactivated IB D1466 and inactivated TRT antigens in W/O emulsion containing 10 µg per dose of CpG. These emulsions were used to vaccinate SPF layers at an age of 14 weeks. Half of the different vaccine groups had been vaccinated at an age of 10 weeks with live IB vaccines. At an age of 26 weeks the chickens were challenged with virulent QX-like IB virus or virulent IB D1466 virus. Between 2 weeks before challenge and 4 weeks after challenge egg production was measured. Furthermore, antibody titers were measured at 7 weeks after vaccination with a serum neutralization test.

As can be seen in the data presented in Table 4 after live priming a clear antibody response could be detected by ELISA. After vaccination with the inactivated vaccines also antibody titers against IB were determined by SN tests. The SN test specifically detects antibodies against IB QX and IB D1466. No cross-reactivity was observed, whereas no distinction can be made between antibodies against IB QX and IB D1466 using ELISA.

The data in Table 7 also show that after challenge there is a very clear drop in the egg production by the virulent IB OX challenge virus in the chickens which had not been vaccinated. Vaccination with live vaccines only, inactivated vaccine only or both results in protective immunity against an egg drop caused by IB QX challenge virus.

TABLE 7

Mean antibody titers to IB, 7 weeks after priming with live vaccines (D98) and 7 weeks after administration of inactivated vaccine (D147) and protection against egg drop by after IB QX or IB D1466 challenges.

| | Vaccines | | Mean arithmetic IB ELISA antibody titer | | | | Mean SNT antibody titers D147*** | | Egg drops by IB QX or IB D1466 |
|---|---|---|---|---|---|---|---|---|---|
| | | | D98 | | D147 | | | | |
| Gr. | Live* | Inactivated# | Titer | Responders | Titer | Responders | IB D1466 | IB QX | |
| 1 | + | High dose | 5385[A] | 40/40[1] | 18620[A] | (20/20)[1] | 9.25[A] (10, 10, 9, 8) | 10.75[A] (11, 12, 10, 10) | −3.9% QX |
| 2 | + | Low dose | 5235[AB] | 40/40[1] | 15532[B] | (20/20)[1] | 9.25[A] (8, 10, 9, 8) | 9.75[AB] (10, 9, 10, 10) | 2.5% QX |
| 3 | + | None | 4161[B] | 40/40[1] | 872[C] | (2/20)[2] | 4[B] (4, 4, 4, 4) | 7.75[B] (10, 8, 6, 7) | −3.2% QX |
| 4 | − | High dose | 22[A] | 0/40[1] | 10520[A] | (20/20)[1] | 9.5[A] (9, 12, 8, 9) | 8.25[A] (6, 8, 9, 10) | −0.8% QX |
| 5 | − | Low dose | 27[A] | 0/40[1] | 8850[A] | (20/20)[1] | 8.75[A] (9, 12, 9, 8) | 9.5[A] (10, 11, 9, 8) | 1.8% QX |
| 6 | − | None | 36[A] | 1/40[1] | 123[B] | (1/20)[2] | 4.25[B] (5, 4, 4, 4) | 4.25[B] (4, 4, 4, 5) | −24.0% QX |

TABLE 7-continued

Mean antibody titers to IB, 7 weeks after priming with live vaccines (D98) and 7 weeks after administration of inactivated vaccine (D147) and protection against egg drop by after IB QX or IB D1466 challenges.

| | Vaccines | | Mean arithmetic IB ELISA antibody titer | | | | Mean SNT antibody titers D147*** | | Egg drops by IB QX or |
|---|---|---|---|---|---|---|---|---|---|
| | | | D98 | | D147 | | | | |
| Gr. | Live* | Inactivated# | Titer | Responders | Titer | Responders | IB D1466 | IB QX | IB D1466 |
| 7 | + | High dose | | | 14652$^B$ | 20/20$^1$ | 9.75$^A$ (9, 9, 10, 11) | 11.5$^A$ (11, 11, 12, 12) | 5.7% D1466 |
| 8 | + | Low dose | | | 16457$^A$ | 20/20$^1$ | 9$^A$ (8, 9, 10, 9) | 10$^A$ (8, 10, 11, 11) | 13.8% D1466 |
| 9 | + | None | | | 1139$^C$ | 20/20$^1$ | 4.5$^B$ (4, 4, 5, 5) | 7$^B$ (7, 7, 8, 6) | 0.8% D1466 |
| 10 | − | High dose | | | 9552$^A$ | 20/20$^1$ | 8.5$^A$ (8, 8, 10, 8) | 9$^A$ (8, 9, 10, 9) | 0% D1466 |
| 11 | − | Low dose | | | 7762$^A$ | 20/20$^1$ | 8.75$^A$ (7, 9, 10, 9) | 8.5$^A$ (8, 8, 9, 9) | 2.3% D1466 |
| 12 | − | None | | | 59$^B$ | 0/20$^2$ | 4.25$^B$ (4, 5, 4, 4) | 4.25$^B$ (4, 4, 5, 4) | −8.3% D1466 |

High dose: $10^{8.0}$ EID$_{50}$ IB QX and $10^{6.8}$ EID$_{50}$ IB D1466, low dose: $10^{7.4}$ EID$_{50}$ IB QX and $10^{6.2}$ EID$_{50}$ IB D1466; $10^{5.3}$ TCID$_{50}$ TRT per dose at 112 days of age.
*POULVAC ® IB Primer in a single dose at 10 weeks of age and POULVAC ® IB QX in a single dose at 12 weeks of age.
**Different letters in each cell indicate that the difference in mean titer is significant (P < 0.05) between each block of 3 groups.
***IB QX and IB D1466 challenge administered at 147 days of age. The cut-off for a positive response was >5.

Further, it was previously thought that an inactivated IB QX antigen is hardly capable to induce antibody titers in chickens after vaccination, unlike non-QX strains of IB. For example, currently marketed products containing antigens from other, non-QX, strains of infectious bronchitis (e.g., IB M41, or IB D274, or IB D1466) are adjuvanted with oil emulsion without CpG and yet elicit sufficient protection. In contrast, as demonstrated in Table 8, oil emulsion without CpG is insufficient to elicit neutralizing antibodies, while addition of CpG results in a robust antibody response.

TABLE 8

Antibody responses in 4-week old SPF chickens against the single inactivated IB QX antigens in a water-in-oil emulsion containing CpG

| IB QX strain | $^{10}$log $EID_{50}$ per dose | Inactivant | CpG per dose | Serological test . . . at . . . days after vaccination: ELISA at 35 | ELISA at 49 | ELISA at 85 | SN test at 35 |
|---|---|---|---|---|---|---|---|
| L1148 | 8.0 | Formol | | 2.477 | 2.928 | 3.573 | 0.0 |
| L1148 | 8.0 | Formol | 5 μg | 3.460 | 3.924 | 4.047 | 5.0 |
| L1148 | 8.0 | BPL | | 2.179 | 2.444 | 2.861 | 3.0 |
| L1148 | 8.0 | BPL | 5 μg | 3.203 | 3.809 | 3.939 | 4.4 |
| L1148 | 7.2 | Formol | | 1.395 | 0.976 | 2.314 | 0.8 |
| L1148 | 7.2 | BPL | | 1.940 | 2.185 | 3.124 | 0.0 |
| 1449-2 | 7.2 | Formol | | 1.628 | 2.994 | 3.397 | 3.0 |
| 1449-2 | 7.2 | BPL | | 2.531 | 2.769 | 3.439 | 3.7 |
| 1449-2 | 7.2 | BPL | 5 μg | 2.774 | 3.191 | 3.621 | 4.3 |
| None | Placebo | | | 1.793 | 0.000 | 1.191 | 0.0 |

At the same time, as noted above, known vaccine strains of IB viruses have proven insufficient to protect against infectious bronchitis caused by IB-QX and IB-QX-like viruses. See WO2010017440. Surprisingly, the vaccines of the instant invention elicited a clear antibody response against the inactivated IB QX antigens.

Example 5. Vaccine Against Infectious Bronchitis, Newcastle Disease, TRT, Infectious Bursal Disease, and Reovirus Mixed sex newborn SPF Leghorn chickens were used in this experiment. Chickens were fed standard diet with water ad libitum.

On day 0, the birds were vaccinated against Infectious Bronchitis with a vaccine containing Massachusetts 1 strain via ocular administration. On day 28 of the experiment, the birds were administered POULVAC® REO and POULVAC® TRT vaccines at dosages recommended by the manufacturer into the birds' wings and eyes, respectively. On day 49 of the experiment, the birds were administered the experimental vaccines. Groups T01, T02, T04, and T05 had 32 birds per group. Groups T03, T06, and T07 had 13 birds per group.

TABLE 9

Experimental vaccine compositions

| Group | Antigen component | Adjuvant |
|---|---|---|
| T01 | IB (106.9 EID (egg infectious dose)$_{50}$), Reo 1733 and Reo2408 ($10^{6.9}$ TCID$_{50}$ total), IBD Lukert ($10^{7.5}$ TCID$_{50}$), IBD 28-1 ($10^{2.95}$ TCID$_{50}$) Newcastle ($10^{8.1}$ EID$_{50}$), TRT ($10^{6.40}$ TCID$_{50}$) | W/O emulsion (Mineral oil ~49.9% v/v, emulsifiers (TWEEN ® 80 and ARLACEL ® total ~9.1% v/v) + 10 µg/g CpG (SEQ ID NO: 8, 65% purity) |
| T02 | IB ($10^{6.9}$ EID$_{50}$), Reo 1733 and Reo2408 ($10^{6.9}$ TCID$_{50}$ total), IBD Lukert ($10^{8.0}$ TCID$_{50}$), IBD 28-1 ($10^{2.95}$ TCID$_{50}$) Newcastle ($10^{8.1}$ EID$_{50}$), TRT ($10^{6.40}$ TCID$_{50}$) | As in T01 |
| T03 | Negative control (no antigens) | W/O emulsion as in T01 – no CpG |
| T04 | As in T01 | W/O emulsion as in T01 – no CpG |
| T05 | As in T02 | W/O emulsion as in T01 – no CpG |
| T06 | MATERNAVAC ® DUO – IBDV + Reo | Commercial Product |
| T07 | MSD-Nobilis (reference TRT) (IB, Newcastle, IBDV, TRT) | Commercial product |

Commercial name of MSD vaccine: Nobilis ® RT+ IBmulti + G + ND

All antigens used in T01, T02, T04, and T05 were inactivated in formaldehyde.

Groups T01-T05 received a 0.5 ml intramuscular injection in the breast area. Groups T06 and T07 were treated according to the manufacturers' protocols.

Blood was taken from the birds on days 70 and 77 for serology analysis. The analysis was performed by serum neutralization test (IB, IBDV, Reo), HAI test (Newcastle), and ELISA (TRT). Serology data for T01, T02, T04 and T05 was analyzed using general linear mixed model with repeated measures. Appropriate log transformation was applied. Model included fixed effects of treatment, time point and treatment by time point interaction and random effects of block and animal within block and treatment (animal term).

(Back-transformed) least square means and 90% confidence intervals were reported along with range of the raw data. If the main effect of treatment or the treatment by time interaction was significant (P 0.10) then comparisons between all treatment groups at each time point were conducted and reported. Treatment groups T03, T06 and T07 were summarized with geometric means, standard errors, and ranges.

The results are provided in Table 10.

perspective, these results demonstrate that decrease of IBD Lukert dose from $10^8$ TCID$_{50}$ to $10^{7.5}$ TCID$_{50}$ (about three-fold reduction) and addition of CpG (compare T01 and T05) to the formulation resulted in increased responses to IBD. Responses to Newcastle, reovirus, and TRT were also increased and the response to IB was not statistically decreased.

Further, the responses to all viruses resulted in protective titers (protective titer for IB is 20, protective titer to Newcastle is 16, protective titer for IBD is 32, protective titer for Reovirus is 16). Efficiency of TRT vaccine is measured by seroconversion. Seroconversion over 70% indicated that the vaccine was effective.

In the experiments above, the formulations containing CpG (groups T01 and T02) were both effective against TRT (over 90% seroconversion). In contrast, the formulations lacking CpG (groups T04 and T05) were not effective against TRT (seroconversion of 62.5% and below).

Group T06 was used as a positive control for IBDV. As shown in Table 10, the titers elicited by vaccine T02 were comparable to the titers elicited by the positive control. Group T07 was used as a positive control for TRT. As shown in Table 10, the experimental vaccines T01 and T02 elicited higher TRT titers than T07.

TABLE 10

Antibody titer, back transformed geometric means

| | Bronchitis | | Newcastle | | IBD | | Reo | | TRT conversion, % | | TRT* | |
|---|---|---|---|---|---|---|---|---|---|---|---|---|
| | D70 | D77 | D70 | D77 | D70 | D77 | D70 | D77 | D70 | D77 | D70 | D77 |
| T01 | 99$^a$ | 83$^a$ | 89$^a$ | 99$^a$ | 4401$^a$ | 3701$^b$ | 484$^a$ | 374$^{ab}$ | 90.6 | 93.7 | 3684$^a$ | 5598$^b$ |
| T02 | 92$^a$ | 76$^a$ | 88$^a$ | 109$^a$ | 6499$^a$ | 9190$^a$ | 641$^a$ | 505$^a$ | 96.8 | 100 | 6155$^a$ | 7971$^a$ |
| T03 | 10 | 9 | 0 | 0 | 0 | 0 | 1 | 1 | — | — | 0 | 0 |
| T04 | 160$^a$ | 144$^a$ | 23$^b$ | 29$^b$ | 528$^c$ | 1367$^c$ | 222$^b$ | 258$^{bc}$ | 40.6 | 46.8 | 68$^c$ | 123$^b$ |
| T05 | 175$^a$ | 102$^a$ | 21$^b$ | 27$^b$ | 970$^b$ | 2201$^{bc}$ | 168$^b$ | 208$^c$ | 62.5 | 62.5 | 342$^b$ | 445$^c$ |
| T06 | 13 | 16 | 0 | 0 | 3527 | 7845 | 713 | 712 | — | — | 0 | 0 |
| T07 | 3719 | 2069 | 243 | 460 | 3005 | 7437 | 0.5 | 0.5 | — | — | 24 | 239 |

Statistical analysis was done comparing the titers elicited by Treatments T01, T02, T04 and T05.
Different letters indicate significant difference (p ≤ 0.1).
TRT* indicates that the titer was obtained using ELISA.
All other results were obtained using by serum neutralization test (IB, IBDV, Reo) or HAI test (Newcastle)

These results demonstrate that addition of CpG to W/O emulsion resulted in almost 3-fold increased immune response to IBDV. Looking at the results from a different In sum, addition of CpG into the W/O emulsion allowed creation of pentavalent vaccine effective against Bronchitis, Newcastle disease, TRT, Infectious Bursal Disease (IBD or Gumboro), and Reovirus. The formulations without CpG were not effective against TRT. In addition, the titers against Newcastle, Reovirus, and IBD were lower in the formulations without CpG than in formulations with CpG.

Example 6. Vaccine Against Infectious Bronchitis, Coryza, Egg Drop Syndrome, Newcastle Disease, and TRT Mixed sex newborn SPF Leghorn chickens were used in this experiment. Chickens were fed standard diet with water ad libitum.

On day 0, the birds were vaccinated against Infectious Bronchitis with a vaccine containing Massachusetts 1 strain via ocular administration. On day 14 of the experiment, the birds were administered POULVAC® TRT vaccines at dosages recommended by the manufacturer intraocularly. On day 35 of the experiment, the experimental vaccines were administered via intramuscular injections.

Table 11 illustrates experimental and control vaccine compositions used in these experiments. Each of the group contained 56 birds.

TABLE 11

Experimental vaccine compositions

| Group | Antigen | Adjuvant |
|---|---|---|
| T01 | None | None (Saline) |
| T02 | POULVAC® MIX 6 (IBK ($10^{6.90}$ $EID_{50}$), Coryza M, Coryza 221, Coryza S (total $10^{6.88}$ $EID_{50}$)), EDS* (80.00 HA units), Newcastle ($10^{8.45}$ $EID_{50}$) | Proprietary |
| T03 | IBK ($10^{6.90}$ $EID_{50}$), TRT ($10^{6.00}$ $TCID_{50}$), Coryza M, Coryza 221, Coryza S (total $10^{6.88}$ $EID_{50}$), EDS (88.00 HA units), Newcastle ($10^{8.43}$ $EID_{50}$) | W/O emulsion (Mineral oil ~51.6% v/v, emulsifiers (TWEEN® 80 and ARLACEL® total ~8.4% v/v) |
| T04 | IBK ($10^{6.90}$ $EID50$), TRT ($10^{6.00}$ $TCID_{50}$), Coryza M, Coryza 221, Coryza S (total $10^{6.88}$ $EID_{50}$), EDS (88.00 HA units), Newcastle ($10^{8.43}$ $EID_{50}$) | As in T03 + 10 μg CpG (SEQ ID NO: 8, 65% purity) |
| T05 | IBK ($10^{6.90}$ $EID_{50}$), TRT ($10^{6.50}$ $TCID_{50}$), Coryza M, Coryza 221, Coryza S (total $10^{6.88}$ $EID_{50}$), EDS (88.00 HA units), Newcastle ($10^{8.43}$ $EID_{50}$) | As in T03 |
| T06 | IBK ($10^{6.90}$ $EID_{50}$), TRT ($10^{6.50}$ $TCID_{50}$), Coryza M, Coryza 221, Coryza S total $10^{6.88}$ $EID_{50}$), EDS (88.00 HA units), Newcastle ($10^{8.43}$ $EID_{50}$) | As in T04 |

*EDS refers to Egg-Drop Syndrome, IBK refers to Infectious Bronchitis

All antigens used in T01, T02, T04, and T05 were inactivated in formaldehyde.

Blood was taken from the birds on days 56 and 70 for serology analysis. Ten percent two sided significance level was used in the analysis.

Serology data for T01, T03, T04, T05 and T06 was analyzed using general linear mixed model with repeated measures. Appropriate log transformation was applied. Model included fixed effects of treatment, time point and treatment by time point interaction and random effects of block and animal within block and treatment (animal term).

(Back-transformed) least square means and 90% confidence intervals were reported along with range of the raw data. If the main effect of treatment or the treatment by time interaction was significant ($P \leq 0.10$) then comparisons between all treatment groups at each time point were conducted and reported. Serology for T02 was summarized with geometric means, standard errors, and ranges.

The results for experimental groups (T03-T06) are summarized in Table 12.

TABLE 12

Antibody titers

| GRP | Bronchitis, SN | | EDS, HAI | | Coryza, SN | | Newcastle, HAI | | TRT, seroconversion % | | TRT, ELISA | |
|---|---|---|---|---|---|---|---|---|---|---|---|---|
| | D56 | D70 | D56 | D70 | D56 | D70 | D56 | D70 | D56 | D70 | D56 | D70 |
| T03 | 78 ± 14[b] | 49 ± 9[b] | 40 ± 7[b] | 111 ± 21[b] | 7 ± 1 | 9 ± 1[b] | 15 ± 2 | 40 ± 4[b] | 39 | 57 | 1527[b] | 1738[c] |
| T04 | 288 ± 44[a] | 141 ± 25[a] | 71 ± 14[a] | 148 ± 30[ab] | 11 ± 1[a] | 18 ± 2[a] | 66 ± 7[b] | 80 ± 9[a] | 86 | 95 | 3199[a] | 4708[a] |

TABLE 12-continued

| | Antibody titers | | | | | | | | | | | |
|---|---|---|---|---|---|---|---|---|---|---|---|---|
| | Bronchitis, SN | | EDS, HAI | | Coryza, SN | | Newcastle, HAI | | TRT, sero-conversion % | | TRT, ELISA | |
| GRP | D56 | D70 | D56 | D70 | D56 | D70 | D56 | D70 | D56 | D70 | D56 | D70 |
| T05 | 70 ± 12 [b] | 44 ± 8 [b] | 40 ± 7 [b] | 103 ± 18 [b] | 5 ± 1 [bc] | 8 ± 1 [b] | 21 ± 2 [c] | 37 ± 4 [b] | 34 | 45 | 1184 [c] | 1279 [d] |
| T06 | 183 ± 33 [a] | 94 ± 18 [a] | 91 ± 19 [a] | 216 ± 44 [a] | 6 ± 1 [b] | 23 ± 3 [a] | 92 ± 10 [a] | 100 ± 11 [a] | 75 | 86 | 2964 [a] | 3641 [b] |

Different letters indicate significant difference ($p \leq 0.1$).

These results demonstrate that addition of CpG to W/O emulsion resulted in 2-3-fold increased immune response to TRT measured by ELISA. Looking at the results from the seroconversion perspective, the groups treated with formulations without CpG (treatments T03 and T05) did not demonstrate efficient TRT seroconversion response (57% or less). In contrast, groups treated with formulations T04 and T06 both of which contained CpG demonstrated efficient seroconversion (75% and above). Even if the dose of TRT antigen was decreased about threefold, addition of CpG more than compensated for the lower antigen dose (compare T04 and T05).

Further, the responses to all viruses resulted in protective titers (protective titer for IB is 20, protective titer to Newcastle is 16, protective titer for Coryza is 5, protective titer for EDS is 18). The SN titers or HAI titers elicited by formulations T04 and T06 (containing CpG) were generally about twice as great as the titers elicited by formulations T03 and T05 (without CpG)

All publications cited in the specification, both patent publications and non-patent publications, are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

The invention claimed is:

1. An immunogenic composition comprising an antigen component and an adjuvant component, wherein:
   a) the antigen component comprises at least one TRT (Turkey Rhinotracheitis) antigen and at least one IB (Infectious Bronchitis) antigen, wherein the at least one IB antigen comprises IB QX antigen;
   b) the adjuvant component comprises an immunostimulatory oligonucleotide and a W/O emulsion, wherein an oil in said W/O emulsion is a non-metabolizable oil.

2. The immunogenic composition of claim 1, wherein the immunostimulatory oligonucleotide is a CpG oligonucleotide that comprises a 5' TLR activation domain and at least two palindromic regions, one palindromic region being a 5' palindromic region of at least 6 nucleotides in length and connected to a 3' palindromic region of at least 8 nucleotides in length either directly or through a spacer, optionally with one or more phosphorothioate bonds.

3. The immunogenic composition of claim 1, further comprising a sterol.

4. The immunogenic composition of claim 3, wherein the sterol is cholesterol.

5. The immunogenic composition of claim 3, essentially free of saponins.

6. The immunogenic composition of claim 3, wherein the sterol is admixed with the immunostimulatory oligonucleotide.

7. The immunogenic composition of claim 1, which is liposome-free.

8. The immunogenic composition of claim 1, wherein the at least one IB antigen further comprises IB D1466 antigen.

9. The immunogenic composition of claim 1, wherein the antigen component further comprises at least one of IB D1466, TRT, Newcastle disease, EDS (Egg Drop Syndrome) and IB M41 antigens.

10. The immunogenic composition of claim 1, wherein the antigen component further comprises at least one of IB M41, IB D274, Newcastle disease LaSota strain, EDS, and TRT antigens.

11. A method of preventing TRT in a poultry animal comprising administering to said poultry animal the immunogenic composition according to claim 1.

12. A method of preventing IB in a poultry animal comprising administering to said poultry animal the immunogenic composition according to claim 1.

13. The method of claim 11, wherein said poultry animal is a chicken.

14. The method of claim 11, which comprises an administration of a primer vaccine prior to the administration of the immunogenic composition according to claim 1.

15. The method of claim 14, wherein the primer vaccine comprises live Infectious Bronchitis virus strain H120 type Massachusetts.

16. A method of preventing IB in a poultry animal comprising administering to said poultry animal a single dose of the immunogenic composition according to claim 1.

17. The immunogenic composition of claim 2, wherein the immunostimulatory oligonucleotide comprises an iodo-modified nucleotide.

* * * * *